United States Patent [19]

Koch

[11] 4,109,382
[45] Aug. 29, 1978

[54] ENOSSAL IMPLANT

[76] Inventor: Werner Lutz Koch, Schwalbenweg 5, 3973 Liebenau, Germany

[21] Appl. No.: 657,582

[22] Filed: Feb. 12, 1976

[30] Foreign Application Priority Data

Feb. 12, 1975 [DE] Fed. Rep. of Germany ....... 2505734
Feb. 13, 1975 [DE] Fed. Rep. of Germany ....... 2505914

[51] Int. Cl.² .............................................. A61C 13/00
[52] U.S. Cl. .................................................. 32/10 A
[58] Field of Search ................ 128/92 E, 92 EB, 305; 32/10 A

[56] References Cited

U.S. PATENT DOCUMENTS

| 2,112,007 | 3/1933 | Adams | 32/10 A |
| 2,224,264 | 12/1940 | Jeanneret | 32/67 |
| 2,634,501 | 4/1953 | Linet | 32/67 |
| 3,011,259 | 12/1961 | Baum | 32/67 |
| 3,436,826 | 4/1969 | Edelman | 32/10 A |
| 3,508,334 | 4/1976 | Weissman | 32/67 |
| 3,623,226 | 11/1971 | Edelman | 32/10 A |
| 3,928,914 | 12/1975 | Kozlousky | 32/10 A |

FOREIGN PATENT DOCUMENTS 2,454,414  5/1975  Fed. Rep. of Germany .......... 32/10 A

OTHER PUBLICATIONS

Oral Implantology by Implants International, Suite 6100, Chrysler Bldg., N.Y., NY, 10017, p. 31, Oct. 1971.

Primary Examiner—Robert Peshock
Attorney, Agent, or Firm—Allegretti, Newitt, Witcoff & McAndrews

[57] ABSTRACT

An enossal implant is disclosed for fastening a firmly seated denture in the mouth. Also disclosed is a template for exact-fit reaming of a slit, a template for exact-fit reaming of a cylindrical hole in the region of the slit, and a setting instrument for setting the implant into the reamed slit and hole.

11 Claims, 19 Drawing Figures

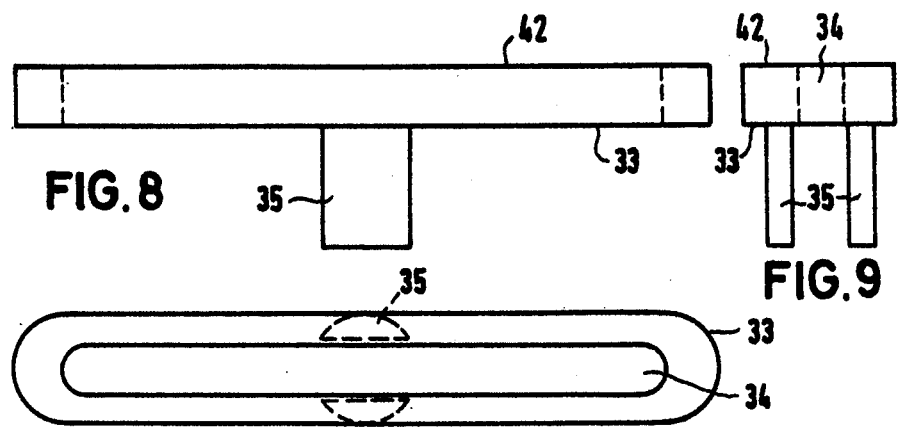
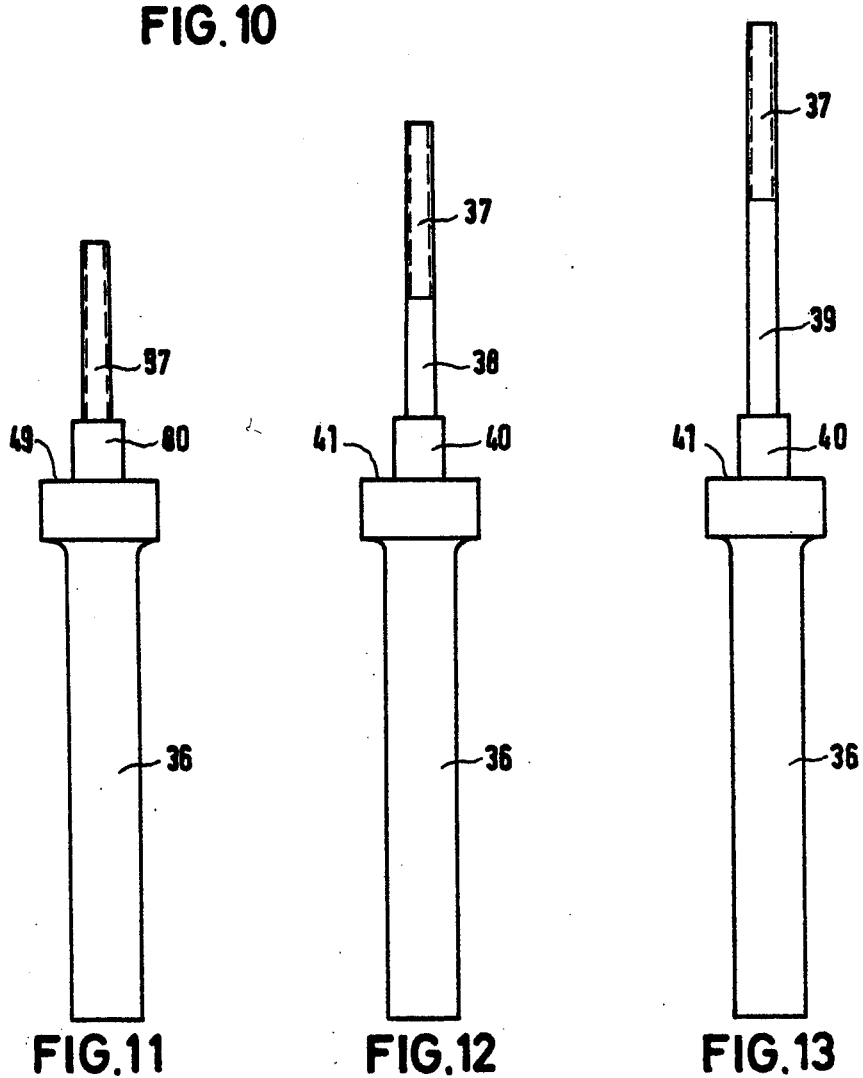

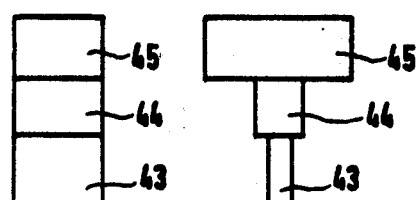
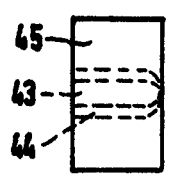
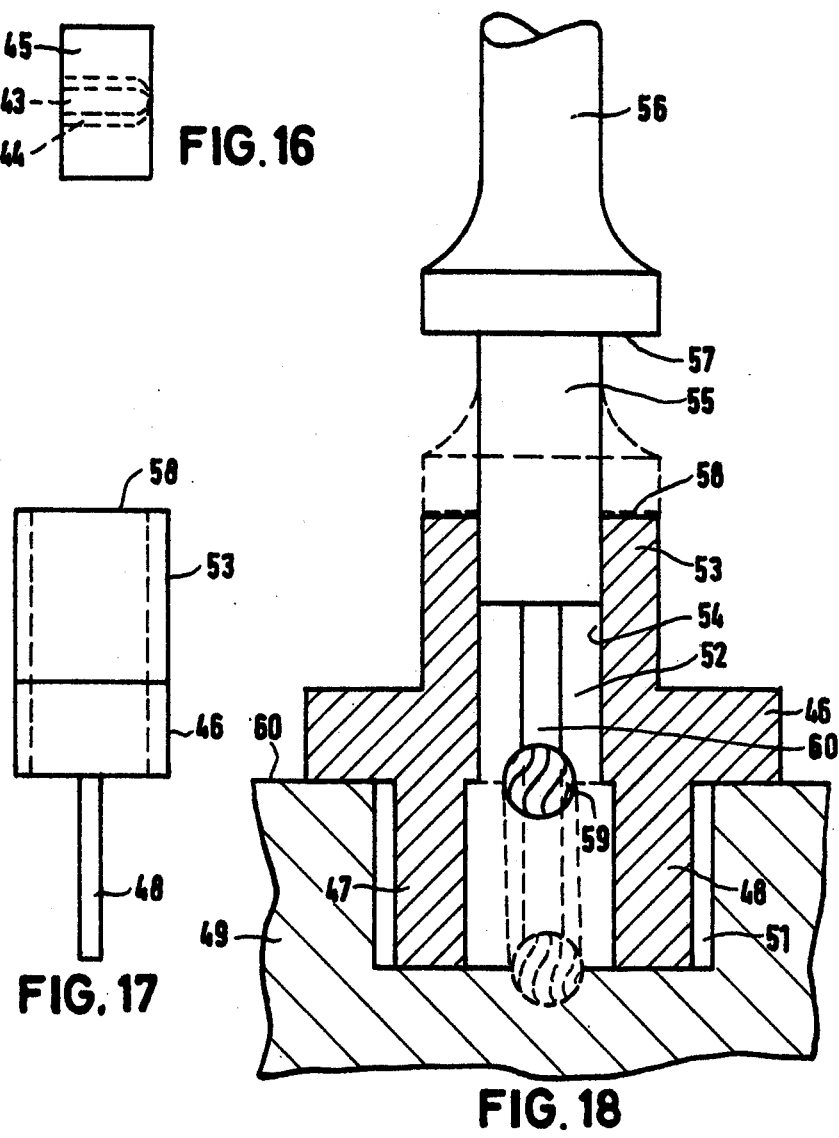

ENOSSAL IMPLANT

BACKGROUND AND SUMMARY OF THE INVENTION

The invention relates to an enossal implant for the fastening of a firmly seated denture in the mouth. The enossal implant includes a post, one end of which serves for the fastening of the firmly seated denture and the other end of which is connected with an anchoring surgically introducible into a jaw bone.

The invention relates, furthermore, to devices for the exact-fit reaming of a slit in a jaw bone and 1 or the exact-fit reaming of a cylindrical hole in the region of the slit in a jaw bone as well as to a setting instrument for driving the enossal implant into the reamings of the jaw bone.

It is known to have an enossal implant for the fastening of firmly seated denture or tooth replacement. This prior implant has a post that is essentially rectangular in its cross section, that tapers upwardly, and that is securely emplaceable on a denture provided with a corresponding recess. The post extends downward into a thin neck and widens, laterally, into a flat, narrow band, from which sharp lashings extend downward. The lashings widen into a swallowtail form, in the plane of the narrow lug, and are made wedge-shaped in its cross section, as well as with depressions for the snug-form embedding in the jaw bone. Underlying this known implant is the thought of using as extensive and sharp a branching as possible of the part of the implant embedded in the jaw bone, in order thereby to achieve a good anchoring or embedding of the implant in the jaw bone. A disadvantage of this known implant lies in that the strip-form part embedded in the jaw bone, from which the lashings extend, is relatively flexible, so that on burdening of the denture, the forces transferred over the neck of the implant to the strip-form part lead to bending of the strip-form part which can result in relative movement of the strip in the jaw bone. Thus there exists the danger of a traumatization of the parts of the jaw bone bordering on the implant. This danger is especially great for the reason that from the strip-form part, the lashes extend away and the ends of the lashes, by reason of the geometrical relations or shapes, move laterally to an increased degree in case of the bending of the strip-form part.

Finally, an appreciable disadvantage with respect to this prior implant lies in that the lashings, extending from the strip-form part into the jaw bone, converge in wedge-form, in the vertical section, and, therefore, form no flat support surfaces by reason of the forces arising in chewing pressure. The wedge-form of the lashings brings about rather, in correspondence to the parallelogram of forces, a pressure increase and thereby an additional loading of the bone tissue. In other words, the wedge-shaped lashings, in the case of chewing pressure, press themselves into the bone tissue in the manner of a wedge.

Underlying the present invention is the problem of providing a firmly-seated denture, in which the disadvantages of the known implant do not occur, in which relative movements of parts of the implant, with respect to one another in the zone of the jaw bone, are reduced to a minimum and in which no high specific surface loads have to be absorbed by the jaw bone tissue. The implant of the present invention, furthermore, is to be easily producible and accurately and securely introducible into the jaw bone. Moreover, there is to be provided the possibility of driving the implant of the present invention accurately and securely into corresponding reamings-out of the jaw bone.

The problem underlying the present invention is solved by novel means wherein the anchoring or embedding means of the implant consists of a cylindrical part running essentially in extension of the post, from which part there extends laterally at least one carrying arm which has, transversely to the axis of the cylindrical part, a slight expansion and in the direction of the axis, a larger expansion.

The cylindrical part of the implant, according to the present invention, provides for a rigid transfer of the burdening forces from the denture to deep into the jaw bone. This rigid part makes possible the fastening of the carrying arms, rigid in respect to the chewing forces. Their rigidity is assured by the great expansion of the part, in direction parallel to the axis of the cylindrical part, so that the forces are transferred from the cylindrical part onto the rigid carrying arms and from these arms to the bone tissue, without there occurring appreciable relative movement between any parts of the implant and the jaw bone. In other words, the use of the improved implant excludes an uneven distribution of forces on the bone tissue in the jaw bone because of the unlikelihood that relative movement between implant and bone tissue will occur when chewing movements occur.

A further advantage of the present invention consists in that the cylindrical part has a threaded bore for releasable fastening of the post which is provided with a threaded pin. This bore can serve for a fastening of the denture, fastened releasably by the doctor but seated firmly for the patient. It can, however, simultaneously serve for the centering of a setting instrument in the setting of the implant in a corresponding reaming-out of the jaw bone.

A still further advantage of the present invention lies in that the narrow edges of the carrying arm of the implant are constructed continuously, without interruptions and in such a manner that the material of the carrying arm, in the zone of the narrow edges, define a carrier having continuous upper and lower trusses. This construction of the carrying arm provides maximum rigidity or stiffness in the carrying arms thereby avoiding the danger of local increases in the specific surface load.

To increase the supporting or engagement surfaces of the carrying arms, on the bone tissue, without giving up the utility of continuous upper and lower trusses of the carrying arms, it is expedient that the carrying arm have recesses in the zone between the border zones of the narrow edges. These recesses can have the form of lengthwise slits whose longest extent is essentially perpendicular to the axis through the cylindrical part. They can also have the form of slits that run substantially parallel to the axis of the cylindrical part. The course of the slits depends on the possible expansion or extension of the carrying arms in a direction parallel to the axis of the cylindrical part. In general, this extension should be as great as possible. It is limited by the vertical extension of the jaw bone and by medical circumstances as well as by the location of the implant in the jaw bone along the rows of teeth.

Another further advantage of the present invention consists in that the cylindrical part has on its end, away from the post, preferably spherical roundings. It is expedient, too, that the narrow edges of the carrying arm or arms and the recesses or slits be rounded. All these roundings bring about, in contrast to the deliberately sharply formed edges of the known implant, as uniform as possible a loading of the bone tissue. Furthermore, it is expedient that the cylindrical part go over into the carrying arms with roundings.

A further advantage of the present invention consists in that the upper edge, facing the post, of the carry arm or arms, runs remote from the upper edge of the cylindrical part facing the post. Thus the cylindrical part projects somewhat beyond the upper edge of the carrying arms so that it can serve for the lateral engagement of a driving-in instrument so that the position of the driving instrument can be fixed relative to the carrying arms.

The improved implant according to the present invention can be introduced especially well into reamings-out of the jaw bone with the aid of a setting instrument. This setting instrument is characterized by a plate from which there projects perpendicularly at least one lug that has a supporting shoulder whose extent, in a direction parallel to the plate, corresponds essentially to the extent of the carrying arm. The plate forms a good attack surface for driving-in instruments, for example, a hammer or the like. Simultaneously the plate makes possible the determination of the penetration depth and the exact position of the implant.

A further advantage of the setting instrument of the present invention consists in that the distance of the support shoulder from the surface of the plate corresponds to the driving-in depth of the implant into the jaw bone. By choice of setting instruments, with differing distance between support shoulder and plate, it is possible to predetermine the driving-in depth of the implant. In the driving-in process, the plate comes into engagement on the upper edge of the jaw bone and thus prevents an undesirably deep or uneven driving in of the implant.

A still further advantage of the setting instrument of the present invention consists in that the plate has a fitting pin means extending in the direction of the lug or lugs, which is conducted through a corresponding recess in the cylindrical part. The fitting pin means has a pin having threads screwable into a central threaded bore of the cylindrical part and engageable slidably into a, fitting bore in the plate. The fitting pin means holds the setting instrument laterally in an exactly fixed position, with respect to the implant, so that damage to the jaw bone is avoided.

The slit in the jaw bone for the implant, according to the present invention, can be made especially accurately by means of an oblong template. The template includes a guide slot corresponding to the length of the slit to be made and has at least one fitting pin for insertion into a fitting hole. The slot is made by means of a reamer which can be installed in a hand piece and which has a cylindrical fitting surface whose diameter corresponds to the width of the guide slot. By the use of such a template, the course of the slit in the jaw bone is firmly prescribed. The position of the template with respect to the jaw bone is determined by a fitting pin, which engages in a corresponding fitting hole. This fitting hole can have a form which corresponds exactly to that of a pin of an implant for fastening a firmly seated denture. Thus no holes or recesses are made in the zone of the jaw bone that are not used later. The cylindrical fitting surface of the reamer is guided exactly by the guide slot so that tiltings are largely avoided.

A further advantage of the present invention consists in that the template has, along the guide slot, a stop surface against which, with reamer fully introduced, an axial stop surface provided on the reamer abuts and thus this structure determines the depth of the slit to be reamed. Through this further advantage, the depth of the slit in the jaw bone is exactly determined by the distance between the front end of the reaming part of the reamer and the axial stop surface. According to this further advantage of the present invention, reamers may be used in which, between the reaming part of the reamer and the axial stop surface, there is arranged a cylindrical shaft whose diameter corresponds to the diameter of the reaming part. Use of several reamers which have cylindrical shafts of varying lengths permits the slit to be slowly enlarged in depth. In this regard, the cylindrical shaft comes into engagement, between the reaming part of the reamer and the axial stop surface, with the walls of the already reamed slit part so that as the depth of the slit increases, the guidance takes place increasingly but not solely by reason of the template, but also by reason of its engagement on the reamed slit. This assures an especially high accuracy of reaming or milling of the slit.

It is expedient that the reaming part of the reamer tapers conically toward the end. As a result of this structure, the reaming part of the reamer is guided with its circumference in the slit being reamed by it. In contrast with a cylindrical construction and because of turning inaccuracies and vibrations, the reamed slit would always be greater than the cylindrical reaming or milling part so that there would be achieved neither an engagement on the rearward cylindrical milling part nor an engagement on the cylindrical shaft.

A still further advantage of this present invention consists in that the fitting pin lies in the zone of the guide slot. The fitting pin has a diameter that is greater than the width of the guide slot, such that the guide slot extends through the fitting pin. With the use of such a fitting pin there is assured the greatest security against turning of the template despite use of only one fitting pin. This is particularly important in, for example, the case of the reaming of a slit into a jaw bone laterally from the gum, wherein the template is aligned through engagement from outside, and especially through engagement on the cut edges of the gum in the zone of the slit to be reamed.

A further advantage of the present invention consists in that a fitting sword is provided whose cross section substantially corresponds to the cross section of the reaming part. The fitting sword is insertable in the guide slots and in the partially reamed slit in such a manner that the template is secured against twistings, the fitting sword filling only a part, preferably less than half, of the guide slot. This fitting sword assures an even better security against twisting. As noted above, the fitting sword fills only a part of the guide slit and of the reamed slit so that in each case, the other part of the slit is free for reaming. When this other part of the slit is reamed or reamed deeper, then the fitting sword can be inserted in this other part so that the reaming can then take place in the part at which previously that fitting sword was inserted.

The present invention relates, furthermore, to a template for the production of a cylindrical hole in the zone of the slit. This template is characterized by a base plate from which there extends on one side, two swords whose cross sections correspond essentially to the width of the reamed slit. Thus, by inserting the swords in the reamed slit, the base plate is fixed on both sides of the cylindrical hole to be made. In the base plate, there is also a cylindrical guide hole for the accurate guidance of a cylindrical finished shaft of a reamer. With this template it is possible, for example, to ream out a hole in the region of the guide slit. The same process used for reaming the slit can be utilized for reaming the fitting hole, namely, introducing fitting parts into parts of the reaming recesses in order then to carry out the reaming operations in the zone not occupied by these fitting parts. As with the template used for the slit, the template for the hole is provided with guide surfaces for the guidance of the reamer which has corresponding cylindrical fitting surfaces. The base plate can, to be sure, depending on the purpose of use, have a different thickness, in order to give the cylindrical guide hole a sufficient guide surface. The base plate can, however, also be arranged so that a fitting sleeve extends on the side away from the fitting swords. The inside wall of this sleeve forms an extension of the guide hole in the base plate and this assures an especially good guidance between reamer and template.

In order to assure a satisfactory guidance over the entire reaming depth, especially even when the reamer is near the reaming depth, it is expedient that the length of the fitting shaft be greater than the depth of the cylindrical hole to be made. It is also expedient that at the root of the fitting shaft, there is an axial stop surface which abuts against a corresponding stop surface on the base plate or the fitting sleeve. This arrangement can thus determine the depth of the cylindrical hole to be made. Moreover, it is expedient that the diameter of the cylindrical fitting shaft of the reamer be greater than the greatest diameter of the reaming, milling head. As a result of this construction, the reaming head can be put through the guide hole of the template without any damage being done to the guide surfaces of the guide hole. An introduction of the reamer with the template installed is also possible.

A still further advantage of the template of the present invention consists in that between the reaming head of the reamer and the fitting shaft, there is a stem zone whose diameter is smaller than the diameter of the reaming head. Through the free space formed in the zone of the stem, the leading off of the reamed material is permitting such that taking the reamer out of the guide hole the material can escape. It is also expedient, however, for the cylindrical fitting shaft to be provided with grooves or holes through which, for example, rinsing fluids can be introduced and the rinsing agent led off, together with the cleared out or reamed out reaming material.

DESCRIPTION OF THE DRAWINGS

With the aid of the drawing, my invention is to be explained in detail with respect to the preferred embodiment of my invention.

FIG. 8 shows a side elevational view of a template of the present invention;

FIG. 9 shows an end plan view of the template according to FIG. 8;

FIG. 10 shows a top plan view of the template according to FIG. 8;

FIGS. 11, 12 and 13 show plan views of reamers of the present invention;

FIG. 14 shows a side view of a sword of the present invention;

FIG. 15 shows a plan, front view of the sword according to FIG. 14;

FIG. 16 shows a top view of the sword according to FIG. 14;

FIG. 17 shows a section through a template for producing a cylindrical hole in the region of a slit with a reaming or milling tool;

FIG. 18 shows a side view of the template according to FIG. 16 with the reaming tool;

DESCRIPTION OF THE PREFERRED EMBODIMENTS

Figure 1:
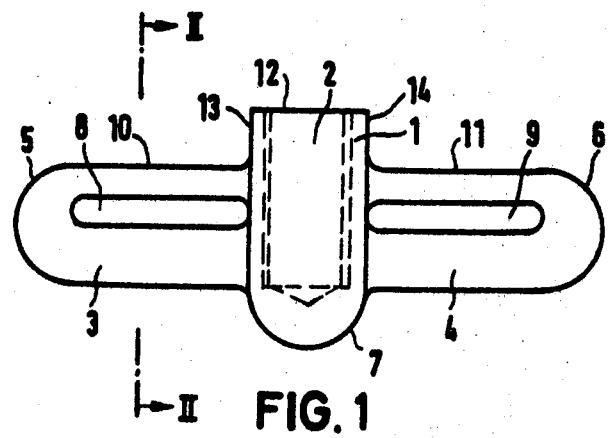
FIG. 1 is a side view of an example of the improved implant of the present invention with two lateral and equal-sized carrying arms.

FIG. 1 shows an improved enossal implant according to the present invention. The implant includes a cylindrical part 1, in which there is a screw threaded bore 2 for the fastening of a denture and from which there extend two carrying arms 3 and 4. The outer ends of the carrying arms 3 and 4 are provided with roundings or rounded ends 5 and 6. The lower end of the cylindrical part 1 is provided with a spherical rounding or rounded end 7.

Figure 2:
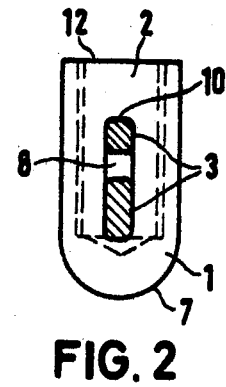
FIG. 2 is a section II—II through FIG. 1.

In the carrying arms 3 and 4, there are slits 8 and 9 which raise the engagement or resting surface on the jaw and which improve the anchoring or embedding of the implant. The edges of the slits 8 and 9 are rounded, just as are the outer edges of the carrying arms 3 and 4, as is to be seen clearly in FIG. 2.

The upper edges 10 and 11 of the carrying arms 3 and 4 are set back with respect to an upper edge 12 of the cylindrical part 1. As a result of this, the upper edge 12 of the cylindrical part may close or be closed off approximately level with the outer surface of a jaw bone, or project only a little over it, while simultaneously the carrying arms 3 and 4 are embedded in the interior of the jaw bone. Furthermore, lateral surfaces 13 and 14 of the projecting cylindrical part 1 provide contact surfaces for a setting instrument.

Figure 3:
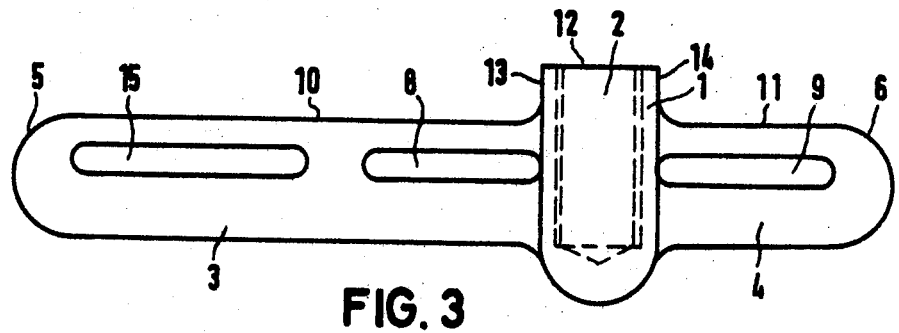
FIG. 3 shows another embodiment of the improved implant of the present invention with two carrying arms of different lengths.

FIG. 3 shows a modification of the embodiment of the implant shown in FIG. 1, in which same parts are provided with the same reference numbers. It is to be perceived that the left carrying arm 3 is longer than the right carrying arm 4. Thus the contact surface of this FIG. 3 implant in the jaw bone and thereby also the anchoring is improved. If need be, this FIG. 3 implant may be adapted to any form of denture, which, for example, may be unsymmetrical in like manner. In the lengthened part of the carrying arm 3 there is provided an additional slit 15. A cross piece 16 is formed between the slit 15 and the slit 8 and in practice, joins the lower truss and the upper truss of the carrying arm 3 so as to thereby increase its rigidity.

Figure 4:
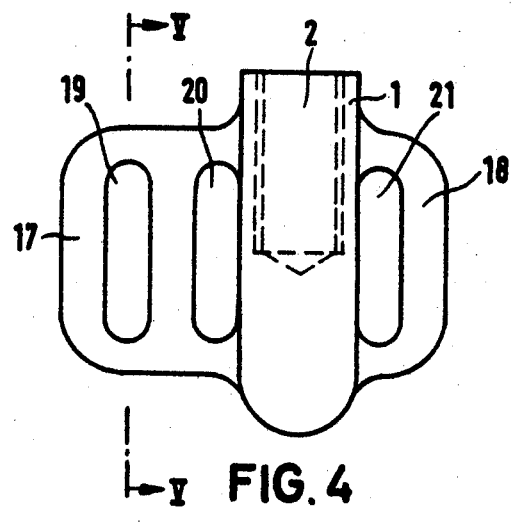
FIG. 4 shows a side view of an improved implant of the present invention with very wide carrying arms.
Figure 5:
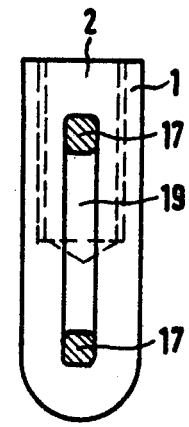
FIG. 5 is a section V—V through FIG. 4.

FIG. 4 shows an embodiment of the implant of the present invention that is similar to the embodiment of FIG. 3 and like parts are provided with like reference numbers. The difference, however, lies in that carrying arms 17 and 18 are made considerably wider and higher than the carrying arms 3 and 4 of the embodiment according to FIG. 3, but simultaneously also shorter in length so that there is given an adaptation to a form of the jaw bone. Slits 19, 20 and 21 run perpendicular and parallel to the axis of the cylindrical part 1. FIG. 5 shows a section V—V through FIG. 4.

Figure 6:
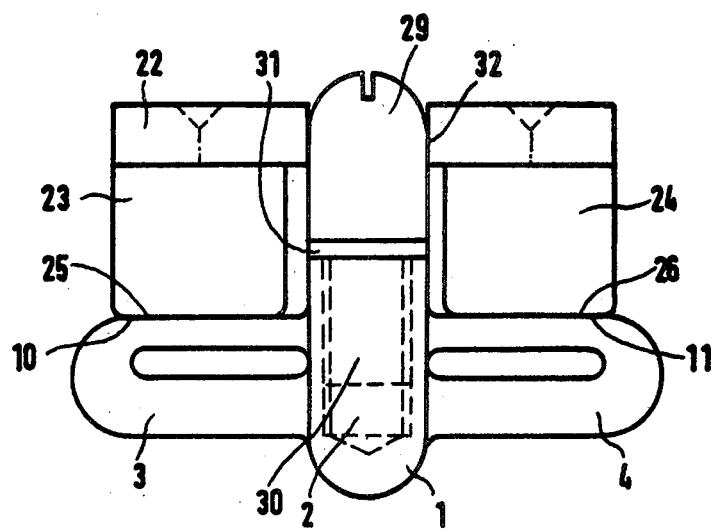
FIG. 6 shows an embodiment of a setting instrument of the present invention together with an implant to be set.

In FIG. 6 there is represented a setting instrument which has a plate 22, from which there extend two lugs or vanes 23 and 24. Support shoulders 25 and 26 are formed on the lugs 23 and 24 and are constructed so that they can be placed on the upper edges 10 and 11 of the implant. The inner edges 27 and 28 of the lugs 23 and 24 are disposed and lie opposite the lateral surfaces 13 and 14 of the cylindrical part 1 of the implant, and thus hold the entire part securely against lateral slipping.

Figure 7:
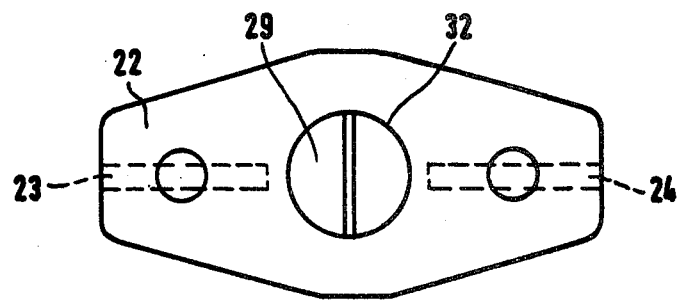
FIG. 7 is a plan view of the setting instrument according to FIG. 6.

In addition, in the embodiment according to FIG. 6, there is provided a fitting pin 29 which includes a threaded pin 30. The pin 30 is screwed into a threaded sleeve 31 and again is screwed into the threaded bore 2 of the implant. In the plate 22 there is a fitting bore 32, by means of which the plate 22, with the lugs 23 and 24, can slide vertically on the fitting pin 29 and thereby be in exact alignment to the implant. FIG. 7 shows a plan view of the embodiment shown from above, in FIG. 6.

In FIGS. 8 to 10, there is shown a template 33, in three different views. Namely, in FIG. 8 in side elevation; in FIG. 9 in plan view; and FIG. 10 in a longwise, top plan view. The template 33 is elongated and has a guide slot 34, the length of which corresponds to the length of the slit to be produced in the jaw bone. In the region of the guide slit 34, there is situated, on the underside of the template 33, a fitting pin 35, which, as is to be perceived clearly from the representation in FIGS. 9 and 10, is likewise slit open in the zone of the guide slot, so that a reamer or reaming or milling tool can be conducted through it freely.

In FIGS. 11 to 13 there are represented various reamers which, in conjunction with the template 33 according to FIGS. 8 to 10, can be utilized to ream slits in the jaw bone in accordance with the principles of the present invention. The reamers in FIGS. 11 to 13 have shafts 36 for insertion in a hand piece of a reaming or milling machine, not shown. The shafts 36 are somewhat tapered conically toward their tips. In the reamers according to FIGS. 12 and 13 there extend behind the reaming parts 37 cylindrical shafts 38 and 39, respectively, of different lengths. All the reamers have cylindrical fitting surfaces 40, whose diameter coincides exactly with the width of the guide slot 34 so that the reaming part 37 is guided by the cylindrical fitting surface 40 in the guide slot 34 in the template 33, whose position, of turn, is determined by the fitting pin 35 which is inserted in a previously bored hole. The axial length of the cylindrical fitting surface 40 determines the effectiveness of the fitting surface during the deep reaming. To be sure, there takes place first of all the sinking of the reamer to its full depth and then the lateral reaming, during which the fitting surfaces 40 are active. It is, of course, also possible to make the axial extent of the fitting surfaces 40 and the correspondingly allocated fitting surfaces of the guide slot 34 correspondingly longer in order, in this way, to achieve better guidances, especially also during the reaming advance in axial direction.

The cylindrical shafts 38 and 39 become effective when the reamer has been introduced to its full depth. The cylindrical shafts 38 and 39 lie laterally against the already reamed walls of the slit to be reamed. Despite the small axial extent of the fitting surfaces 40, the shafts 38 and 39 afford increasing reaming depth and increasing guidance for the reamer. This is of special significance in the reaming of slits in the jaw bone because in the region of the mouth, the height of the template 33 in conjunction with the length of the fitting pin 35, cannot be made arbitrarily large.

The reamers have, furthermore, axial stop surfaces 41, which through stops on an upper surface 42 of the template 33, determine the depth of the reamed slit in each case.

A fitting sword 43, as shown in FIGS. 14 to 16, includes cross section which corresponds, essentially, to the cross section of the reamer, namely to the reaming part 37 or to the cylindrical shafts 38 and 39. The sword 43 has, furthermore, a part 44, the cross section of which corresponds to the width of the fitting slot 34 in the template 33. Furthermore, for manipulation, there is additionally provided a handle 45. The fitting sword 43 can be inserted in a slit which has been reamed, at least in the region of the lateral extent of the sword 43. The sword 43 is inserted to a reduced depth as compared with the overall depth of the slit and, at a point remote from the fitting pin 35. As a consequence of the insertion of the sword 43, the template 33 is secured against rotation so that the further reaming can take place, with the aid of the template and the reamers, without any change in the position of the template with respect to the jaw bone. The slit is then completely executed during which process, the fitting sword 43 is shiftable in such a way that entire region of the slit is fully reamable including that in which the fitting sword 43 was first inserted.

FIG. 17 shows a template for the production of a cylindrical hole in the jaw bone in the region of a slit. This template has a base plate 46, from which there extend downward two swords 47 and 48, whose width corresponds essentially to the width of the reamed slit, therefore to the width of the reaming part 37, 37 and 38, and 37 and 39, respectively, of the reamers according to FIGS. 11 to 13. The swords 47 and 48, accordingly, hold the base plate 46 after their insertion in an exactly fixed position with respect to a jaw bone 49 (only partially represented in FIG. 18), so that the base plate 46 rests on the upper edge 50 of the bone 49. The slit, in which there are inserted the swords 47 and 48, is indicated by the reference number 51.

As shown in FIG. 18, the base plate 46 has a guide hole 57, which is lengthened by an integral fitting sleeve 53, so that there is present a continuously long inner wall 54. This assures an exact guidance of a fitting shaft 55 of a reamer 56 over the entire axial reaming path of the reamer 56. The reamer 56 has an axial stop surface 57, which in the axial introduction of the reamer into the guide hole 52, strikes against an oppositely situated stop surface 58 of the fitting sleeve 53 and thus this limits the depth of the reamed hole. The reaming of the depth of the hole is carried out by a spherical reaming head 59, which is joined over a stem 60 with the fitting shaft 55. The deepest introduction position of the reamer 56 is indicated in FIG. 18 by broken lines.

Figure 19:
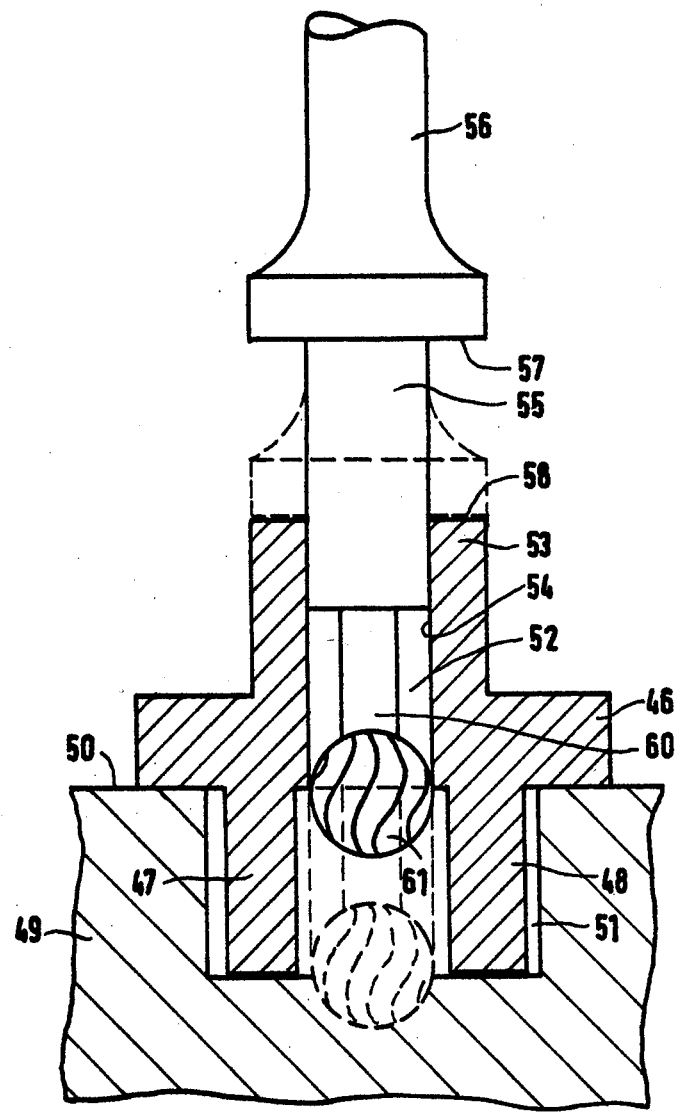
FIG. 19 corresponds to FIG. 16, but there is provided a reaming tool with larger rotary part.

In actual practice, it is expedient that the preparation of a cylindrical hole in a jaw bone does not take place, at first, in the total width of the diameter of the desired hole, but rather with reaming or milling heads of increasing diameters. FIG. 19 shows the embodiment according to FIG. 18, in which like parts are provided with like reference numbers. The sole difference between these two embodiments, lies in that in FIG. 19, there is used a reaming or milling head 61 that has a larger diameter than the reaming head 59. The head 61 corresponds to the diameter of the hole to be made in the jaw bone.

I claim:

1. An improved implant for anchoring a denture, said improved implant being surgically introduceable into a cavity in a jaw bone and comprising, in combination:

a rigid upright cylindrical post of pre-selected height and outer diameter with its longitudinal axis defining a first reference axis, said upright cylindrical post having a bottom end within said cavity when said anchoring member is set in said jaw bone;

at least one rigid, generally planar carrying arm laterally attached to said upright cylindrical post having a pre-selected length in the direction of a second reference axis perpendicular to said first reference axis, a thickness less than said outer diameter of said upright cylindrical post in a direction perpendicular to the plane defined by said first and second reference axes, a top edge and a bottom edge, and a width from said top edge to said bottom edge not greater than the height of said upright cylindrical post in a direction parallel to said first reference axis; and means for fastening said upright cylindrical post of said anchoring member to said denture;

said bottom end of said upright cylindrical post being rounded and extending below said bottom edge of said carrying arm; and said bottom edge of said carrying arm being continuous, flat, substantially unbroken, and said bottom edge lying in a plane substantially perpendicular to said first reference axis.

2. Apparatus for guiding the level setting of an implant in a cavity in a jaw bone, said implant comprising, in combination, an upright cylindrical post of pre-selected height and outer diameter with its longitudinal axis defining a first reference axis and at least one carrying arm laterally attached to said upright cylindrical post having a pre-selected length in the direction of a second reference axis perpendicular to said first reference axis, a thickness in a direction perpendicular to the plane defined by said first and second reference axes, a top edge and bottom edge and a width from said top edge to said bottom edge not greater than the height of said upright part in a direction parallel to said first reference axis, said apparatus comprising, in combination:

a setting instrument having a plate for receiving hammer blows and at least one lug attached to said plate; and means for releasably attaching said plate to said upright cylindrical post of said implant;

said lug resting on said top edge of said carrying arm when said plate is attached to said upright cylindrical post, for transferring a portion of the force of said hammer blows to said carrying arm for level setting of said carrying arm and upright cylindrical post.

3. The apparatus of claim 2 in which said plate defines a first reference plane, said lug having a length in a direction perpendicular to said first reference plane equal to the pre-selected depth to which said top edge of said carrying arm of said implant is to be driven into said jaw bone.

4. The apparatus of claim 2 in which said plate has a fitting bore and said means for releasably attaching said plate to said upright cylindrical post comprises a fitting pin slidably engageable in said fitting bore.

5. The apparatus of claim 2 in which said upright cylindrical post has a threaded bore and said fitting pin has a threaded portion engageable in said threaded bore.

6. Apparatus for installing an implant in a jaw bone comprising, in combination:

a reaming tool having a reaming head and a cylindrical shaft with a first enlarged section having a first pre-selected outer diameter and with a second enlarged section having a second pre-selected outer diameter, said second outer diameter exceeding said first outer diameter, said reaming tool thereby having a shoulder between said first enlarged section and said second enlarged section; and a template for guiding the drilling and reaming of a hole having its center located in a slit in a jaw bone, said drilling template including a base plate defining a cylindrical guide hole for guiding said reaming tool, a plurality of means for steadying said base plate and a stop surface, said means being attached to said base plate on opposite sides of said guide hole and insertable into said slit, said guide hole having an inner diameter substantially equal to the outer diameter of said fitting section, said reaming tool having a length from said reaming head to said shoulder equal to the combined length of said base plate from said means to said stop surface added to the pre-selected depth of said hole to be drilled.

7. Apparatus for guiding a reaming tool for the true-to-measure reaming of a slit in a jaw bone through the region of a fitting hole drilling therein, said slit having a width less than the diameter of said fitting hole, said apparatus comprising a template comprising, in combination:

an elongated plate with a guide slot for guiding said reaming tool; and a cylindrical fitting pin extending from said plate insertable into said fitting hole and having a diameter greater than the width of said guide slot and a passageway for passage of said reaming tool.

8. The apparatus of claim 7 further comprising, in combination with said template:

means insertable into a portion of said slit in said jaw bone through said slot in said template for steadying said template.

9. An improved method for fastening a denture to a jaw bone, said improved method utilizing a template for guiding a reaming tool having an elongated plate with a guide slot for guiding said reaming tool and a fitting pin extending therefrom engageable in said fitting hole for steadying said template, said method comprising, in combination:

producing a fitting hole in said jaw bone at a pre-selected location;

engaging said fitting pin of said template in said fitting hole and aligning said guide slot along said jaw bone;

producing a slit along said jaw bone through the location of said fitting hole, said slit producing step including guiding said reaming tool in said guide slot in said elongated plate of said template;

producing a finished hole at said location of said fitting hole;

setting an anchoring member into said jaw bone in the cavity formed by said slot and hole; and fastening said denture to said anchoring member.

10. The improved method of claim 9 utilizing a drilling template having a base plate with a guide hole for guiding a drilling tool and means insertable in said slit, said method further comprising the step of inserting said means of said drilling template in said slit, said finished hole producing step including guiding said drilling tool in said guide hole of said base plate of said drilling template.

11. The improved method of claim 10 utilizing an anchoring member comprising a rigid upright part of pre-selected height and outer dimension with its longitudinal axis defining a first reference axis, at least one rigid carrying arm laterally attached to said upright part having a pre-selected length in the direction of a second reference axis perpendicular to said first reference axis, a thickness less than said outer dimension or said cylindrical part in a direction perpendicular to the plane defined by said first and second reference axes, a top edge and a bottom edge, and a width from said top edge to said bottom edge not greater than the height of said upright part in a direction parallel to said first reference axis and further utilizing setting apparatus comprising a plate for receiving hammer blows; means for releasably attaching said plate to said upright part of said anchoring member and at least one lug attached to said plate for transferring a portion of the force of said hammer blows to said carrying arm of said anchoring member for level setting of said carrying arm and cylindrical part, said method further comprising the step of attaching said setting apparatus to said anchoring member, said setting step including hammering said setting apparatus to set said anchoring member.

* * * * *